(12) United States Patent
Iwasaki (10) Patent No.: US 10,391,001 B2
(45) Date of Patent: Aug. 27, 2019

(54) ABSORBENT ARTICLE

(71) Applicant: DAIO PAPER CORPORATION, Ehime (JP)

(72) Inventor: Ai Iwasaki, Tochigi (JP)

(73) Assignee: DAIO PAPER CORPORATION, Ehime (JP)

( * ) Notice: Subject to any disclaimer, the term of this patent is extended or adjusted under 35 U.S.C. 154(b) by 125 days.

(21) Appl. No.: 15/552,926

(22) PCT Filed: Mar. 16, 2016

(86) PCT No.: PCT/JP2016/058323
§ 371 (c)(1),
(2) Date: Aug. 23, 2017

(87) PCT Pub. No.: WO2016/148191
PCT Pub. Date: Sep. 22, 2016

(65) Prior Publication Data
US 2018/0028368 A1    Feb. 1, 2018

(30) Foreign Application Priority Data

Mar. 16, 2015   (JP) .................. 2015-051897

(51) Int. Cl.
*A61F 13/472*    (2006.01)
*A61F 13/56*    (2006.01)

(52) U.S. Cl.
CPC .. *A61F 13/47272* (2013.01); *A61F 13/47218* (2013.01); *A61F 13/5611* (2013.01)

(58) Field of Classification Search
CPC .......... A61F 13/47218; A61F 13/47272; A61F 13/5611; A61F 13/472; A61F 13/47236; A61F 13/47245
See application file for complete search history.

(56) References Cited

U.S. PATENT DOCUMENTS 8,691,040 B2    4/2014  Yamamoto
2003/0055392 A1    3/2003  Tagami et al.
(Continued)

FOREIGN PATENT DOCUMENTS

JP    H05-007220 U    2/1993
JP    H05-033721 U    5/1993
(Continued)

OTHER PUBLICATIONS

International Search Report for PCT/JP2016/058323 dated Apr. 19, 2016.

*Primary Examiner* — Kai H Weng
(74) *Attorney, Agent, or Firm* — IPUSA, PLLC (57) ABSTRACT

To surely prevent leakage, not to cause a wearer feel anxiety against the leakage, and to improve fit. There is provided a sanitary napkin (1) in which a convex portion (20) of an absorbent body that is high toward a skin side is formed at a skin side surface of the absorbent body (4) at a center portion in a width direction. The convex portion (20) is constituted by a front convex portion (24) designed to be provided at an area including a body fluid expelling portion of a wearer, a rear convex portion (25) designed to be provided at an area including an intergluteal cleft of the wearer, and a constricted convex portion (23) provided at an area connecting the front convex portion (24) and the rear convex portion (25) in a front-rear direction of a napkin whose both side edges are constricted toward an inner side. In particular, the rear convex portion (25) is designed to be provided at an area from a start position of the intergluteal cleft of the wearer at a crotch side, in a rearward direction, to a position exceeding the intergluteal cleft, an end position of the intergluteal cleft or at a middle position of the intergluteal cleft, the maximum width of the rear convex portion (25) being 20 to 36 mm, and the maximum width of the rear convex portion (25) and the width of the front convex portion (24) being the same width.

2 Claims, 5 Drawing Sheets

(56) References Cited

U.S. PATENT DOCUMENTS

| | | | | |
|---|---|---|---|---|
| 2005/0267435 | A1* | 12/2005 | Tanio | A61F 13/4702 |
| | | | | 604/385.17 |
| 2006/0282059 | A1* | 12/2006 | Fujikawa | A61F 13/47218 |
| | | | | 604/385.17 |
| 2013/0165885 | A1 | 6/2013 | Kurihara | |

FOREIGN PATENT DOCUMENTS

| | | |
|---|---|---|
| JP | H10-328232 | 12/1998 |
| JP | 2003-079662 | 3/2003 |
| JP | 2006-239162 | 9/2006 |
| JP | 2006-346021 | 12/2006 |
| JP | 2007-089906 | 4/2007 |
| JP | 2007-097954 | 4/2007 |
| JP | 2007-143696 | 6/2007 |
| JP | 2007-195665 | 8/2007 |
| JP | 2008-006204 | 1/2008 |
| JP | 2008-055110 | 3/2008 |
| JP | 2008-295475 | 12/2008 |
| JP | 2009-112864 | 5/2009 |
| JP | 2009-207599 | 9/2009 |
| JP | 2010-131297 | 6/2010 |
| JP | 2010-227543 | 10/2010 |
| JP | 2012-050497 | 3/2012 |
| JP | 2012-071102 | 4/2012 |
| JP | 2012-157459 | 8/2012 |

* cited by examiner

| SIZE IN PLANAR VIEW (mm) | EXAMPLE | COMPARATIVE EXAMPLE 1 | COMPARATIVE EXAMPLE 2 |
|---|---|---|---|
| DIMENSIONS OF CONVEX PORTION (cm²) | 58.2 | 60.8 | 46.8 |
| ABSORPTION AMOUNT (g) LIE ON ONE'S RIGHT SIDE | 46.2 | 39.9 | 44.3 |
| ABSORPTION AMOUNT (g) LIE ON ONE'S BACK | 93.3 | 86.2 | 81.7 |

ABSORBENT ARTICLE

BACKGROUND OF THE INVENTION

1. Field of the Invention

The present invention mainly relates to an absorbent article used in sanitary napkins, panty liners, incontinence pads, toiletries and the like, and an absorbent body in which a convex portion of an absorbent body that is high toward a skin side is formed at a skin side surface of the absorbent body at a center portion in a width direction.

2. Description of the Related Art

Conventionally, as absorbent articles such as panty liners, sanitary napkins, incontinence pads and the like, an absorbent article is known in which an absorbent body made of cotton-like pulp or the like is provided between a liquid impermeable backsheet such as a polyethylene sheet or a non-woven-fabric made of laminated polyethylene sheets, and a liquid permeable topsheet such as a non-woven-fabric or a permeable plastic sheet.

Figure 5:
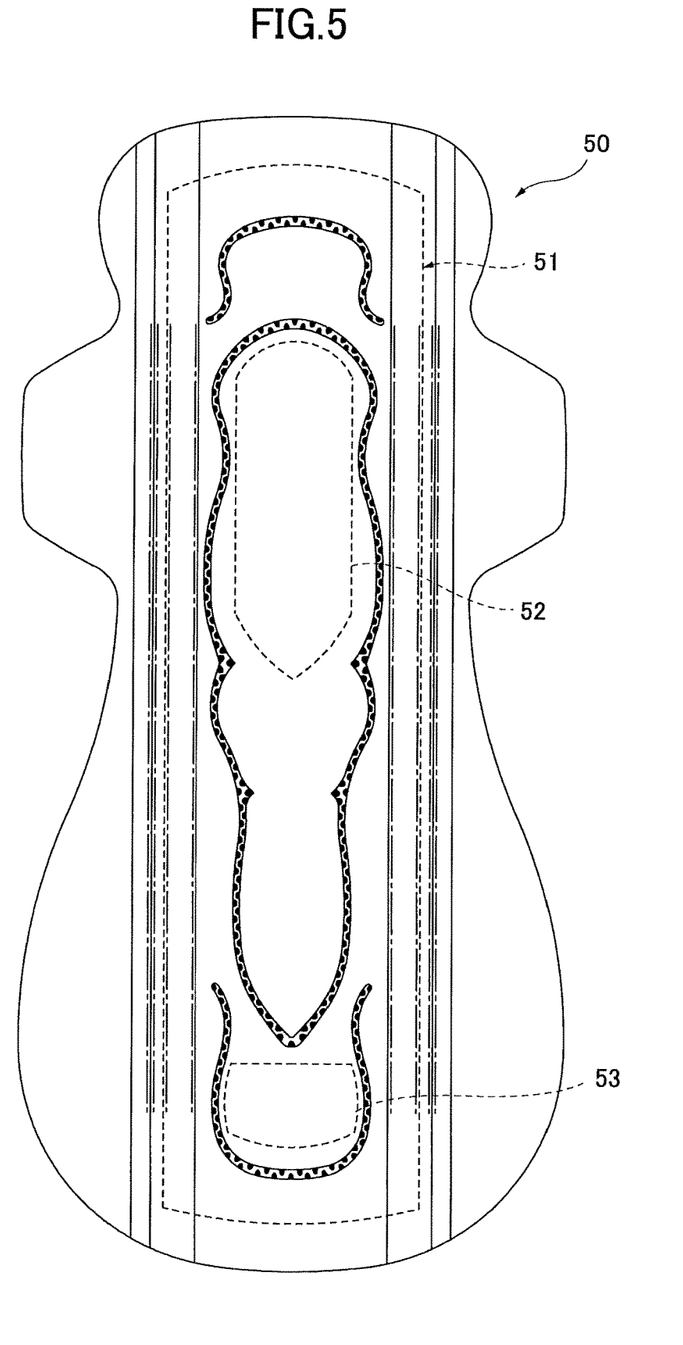
FIG. 5 is a development elevation view of a conventional sanitary napkin 50.

This kind of absorbent article has been improved many times, and various absorbent articles are provided in each of which a convex portion of an absorbent body that is high toward a skin side is formed at a skin side surface of the absorbent body. For example, as illustrated in FIG. 5, following Patent Document 1 discloses a sanitary napkin 50 that includes a front convex portion 52 that protrudes toward a skin contacting surface at an area of the absorbent body 51 corresponding to a menstrual blood expelling port and a rear convex portion 53 that protrudes toward the skin contacting surface at a rear side of an area corresponding to an intergluteal cleft.

Further, following Patent Document 2 discloses an absorbent article in which an absorbent body includes a convex portion whose width is narrower than that of the absorbent body and that protrudes at a skin contacting surface of the absorbent article, wherein the convex portion is constituted by a front convex portion and a rear convex portion that are separately provided at a front portion and a rear portion of the absorbent article, respectively.

[Patent Documents]

Patent Document 1: Japanese Laid-open Patent Publication No. 2012-157459

Patent Document 2: Japanese Laid-open Patent Publication No. 2009-112864

In the absorbent article disclosed in above Patent Document 1 or 2, as illustrated in FIG. 5, as the front convex portion 52 and the rear convex portion 53 are separately provided at front and rear of the absorbent article, respectively, apart from each other, the height at a skin side surface therebetween is relatively low. Here, a main function of the front convex portion 52 is to fit a body fluid expelling portion of a wearer to rapidly absorb expelled body fluid, and a main function of the rear convex portion 53 is to block and absorb the body fluid that is flowed rearward at a space between a skin surface and a front surface of the absorbent article along skin.

In order to retain a sufficient absorption amount, the amount of pulp may be increased for the front convex portion. However, at the front convex portion, there is a limitation in height toward the skin surface due to ensuring a proper fit. Thus, there is no means to retain a sufficient amount of pulp, except by spreading the width of the front convex portion. Thus, there is a case that both side edges of the front convex portion are formed near standing gathers, respectively, and the body fluid absorbed in the front convex portion easily adheres to the standing gathers. If the body fluid adheres the standing gathers, there is a risk that a wearer may feel anxiety that leakage is about to occur by seeing diffusion of the body fluid after used.

Further, as the height of the absorbent body toward the skin side is low at a portion between the front convex portion and the rear convex portion, there is a risk that adhesion between the front surface of the absorbent article and the skin surface is lowered, and the body fluid flows rearward along the skin. If the body fluid flows along the skin, a wearer may feel anxiety against leakage, and there is a risk, if the absorbent article is twisted or shifted when attached, that the body fluid flowed rearward cannot be blocked and absorbed by the rear convex portion and leakage occurs.

Further, when used, the rear convex portion contacts a portion near the tailbone to cause unconformable feeling for a wearer.

SUMMARY OF THE INVENTION

Thus, the present invention is made in light of the above problems, and provides an absorbent article by which leakage is surely prevented, a wearer can be free from anxiety against the leakage, and fit is improved.

In order to solve the above problem, as the invention of claim 1, there is provided an absorbent article including: an absorbent body provided between a liquid permeable topsheet and a backsheet, a convex portion of an absorbent body that is high toward a skin side being formed at a skin side surface of the absorbent body at a center portion in a width direction, wherein the convex portion includes
a front convex portion designed to be provided at an area including a body fluid expelling portion of a wearer,
a rear convex portion designed to be provided at an area including an intergluteal cleft of the wearer, and
a constricted convex portion provided at an area connecting the front convex portion and the rear convex portion in a front-rear direction of the absorbent article whose both side edges are constricted toward an inner side, wherein the front convex portion is formed to be vertically long in the front-rear direction of the absorbent article, both side edges of the front convex portion being formed by linear lines extending in the front-rear direction of the absorbent article, the width of the front convex portion being the same over the entire length, the width of the front convex portion being 20 to 36 mm, wherein the rear convex portion is designed to be provided at an area from a start position of the intergluteal cleft of the wearer at a crotch side, in a rearward direction, to a position exceeding the intergluteal cleft, an end position of the intergluteal cleft or a middle position of the intergluteal cleft, the maximum width of the rear convex portion being 20 to 36 mm, the maximum width of the rear convex portion and the width of the front convex portion being the same width, and wherein both side edges of the constricted convex portion are formed by arc-shaped curves each having a center at outside in the width direction, an interface of the constricted convex portion with the front convex portion being provided at an area corresponding to a perineum portion of the wearer, the minimum width of the constricted convex portion being 10 to 20 mm, the length of the constricted convex portion in the front-rear direction being 45 to 75% of the length of the front convex portion in the front-rear direction.

According to the invention of claim 1, the convex portion of the absorbent body is constituted by the front convex portion corresponding to the body fluid expelling portion, the rear convex portion corresponding to the intergluteal cleft, and the constricted convex portion provided at the area connecting the front convex portion and the rear convex portion in the front-rear direction of the absorbent article whose both side edges are constricted toward the inner direction. Thus, by providing the constricted convex portion between the front convex portion and the rear convex portion, the body fluid absorbed in the front convex portion can be diffused in the entirety of the convex portion including the constricted convex portion and the rear convex portion, the body fluid can be efficiently absorbed in the convex portion, and leakage of the body fluid can be prevented. Further, as the body fluid absorbed in the front convex portion diffuses in the entirety of the convex portion including the constricted convex portion and the rear convex portion and sufficient absorption volume can be ensured by the entirety of the convex portion, it is unnecessary to form the front convex portion to be wide, and the body fluid can be suppressed from being diffused near standing gathers at both side portions. As a result, a wearer hardly feels anxiety against the leakage.

The front convex portion is formed to be vertically long in the front-rear direction of the absorbent article, both side edges of the front convex portion being formed by linear lines extending in the front-rear direction of the absorbent article, the width of the front convex portion being the same over the entire length, the width of the front convex portion being 20 to 36 mm. Thus, the front convex portion can easily fit the body fluid expelling portion of the wearer, the body fluid can be surely absorbed in the front convex portion, diffusion of the body fluid in the width direction is suppressed in the front convex portion, and diffusion of the body fluid in the rearward direction easily occurs.

The rear convex portion is designed to be provided at an area from a start position of the intergluteal cleft of the wearer at a crotch side, in a rearward direction, to a position exceeding the intergluteal cleft, an end position of the intergluteal cleft or a middle position of the intergluteal cleft, the maximum width of the rear convex portion being 20 to 36 mm, the maximum width of the rear convex portion and the width of the front convex portion being the same width. With this, sufficient absorption volume can be retained at the rear convex portion, and the body fluid diffused from the front convex portion can be sufficiently absorbed.

The both side edges of the constricted convex portion are formed by arc-shaped curves each having a center at outside in the width direction and an interface of the constricted convex portion with the front convex portion is provided at an area corresponding to a perineum portion of the wearer. By forming both side edges by the arc-shaped curves each having a center at outside in the width direction, the diffusion of the body fluid in the rearward direction is hardly lowered in the constricted convex portion, and the constricted convex portion easily fits the body.

By providing the constricted convex portion, the absorbent body is formed to be a convex that protrudes toward the skin side at the portion connecting the front convex portion and the rear convex portion. Thus, a space is generated between the body fluid expelling portion and the intergluteal cleft between the skin surface and the front surface of the absorbent article, and the body fluid is prevented from flowing along skin. With this, leakage of the body fluid can be surely prevented, and a wearer can be free from anxiety against the leakage.

Further, as the constricted convex portion is formed such that both side edges are constricted toward the inner direction, the constricted convex portion can enter a narrow groove or a small concave portion of the body without a space, and the body fluid that flows along the skin is hardly generated.

As the interface of the front convex portion and the constricted convex portion is provided at the area corresponding to the perineum portion of the wearer, the constricted convex portion can fit the skin surface from the perineum portion toward backside, and leakage of the body fluid can be furthermore surely prevented.

The minimum width of the constricted convex portion is 10 to 20 mm, and the length of the constricted convex portion in the front-rear direction is 45 to 75% of the length of the front convex portion in the front-rear direction. Thus, the constricted convex portion can surely fit the skin surface.

As the invention of claim 2, there is provided the absorbent article according to claim 1, wherein the rear convex portion is formed in a tapered shape whose width is gradually narrowed toward a rear direction of the absorbent article.

According to the invention of claim 2, the rear convex portion is formed in the tapered shape whose width is gradually narrowed toward the rear direction of the absorbent article. Thus, the rear convex portion easily enters the intergluteal cleft, and the leakage of the body fluid along the intergluteal cleft can be prevented.

As described above in detail, according to the invention, leakage can be surely prevented, a wearer can be free from anxiety against the leakage, and fit can be improved.

DETAILED DESCRIPTION OF THE PREFERRED EMBODIMENTS

Hereinafter, embodiments of the present invention are described in detail with reference to drawings. (Basic structure of sanitary napkin 1)

Figure 1:
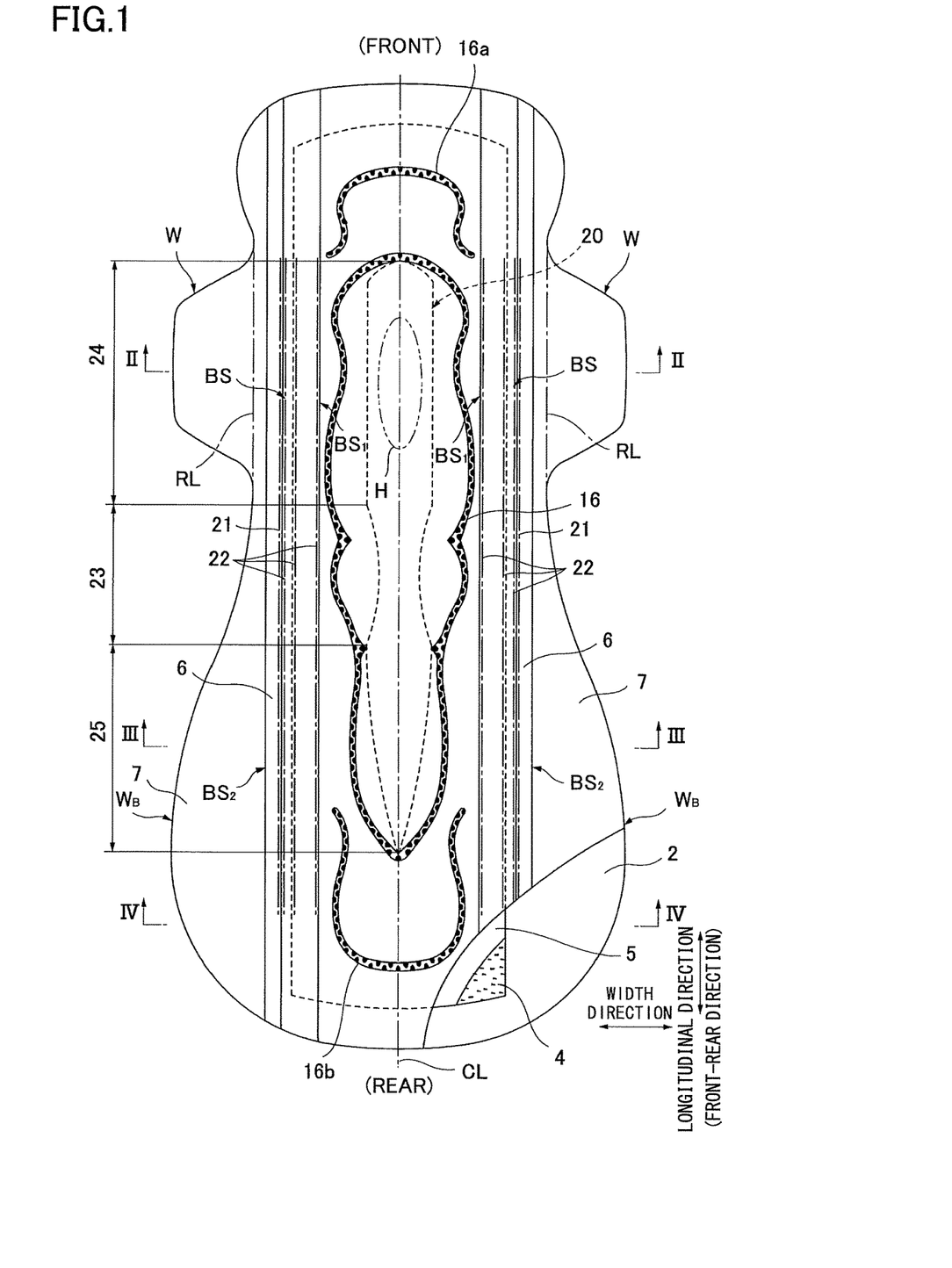
FIG. 1 is a partially cutaway development elevation view of a sanitary napkin 1 of the invention.

The sanitary napkin 1 is mainly constituted of a liquid impermeable backsheet 2 made of a polyethylene sheet or the like, a liquid permeable topsheet 3 that allows menstrual blood, vaginal discharge or the like (hereinafter, referred to as "body fluid".) to rapidly permeate, an absorbent body 4 made of cotton-like pulp, synthetic pulp or the like and provided between the sheets 2 and 3, an encapsulating sheet 5, made of a crepe paper, a non-woven-fabric or the like, that surrounds the absorbent body 4 for retaining the shape and improving the diffusion of the absorbent body 4, non-woven-fabrics 6 for forming a pair of standing gathers BS, BS matched in a lateral direction that protrude toward a front surface side in a predetermined zone in a front-rear direction including at least a blood expelling portion H, while standing from approximate side edge portions of the absorbent body 4, side non-woven fabrics 7 provided outside of the standing gathers BS, BS along a napkin longitudinal direction (hereinafter, referred to as a "napkin front-rear direction" as well.), and a convex portion 20 of an absorbent body that is high toward a skin side, provided at a skin side surface of the absorbent body 4 along the napkin longitudinal direction at a center portion in a width direction. Around the absorbent body 4, outer end portions of the liquid impermeable backsheet 2 and the liquid permeable topsheet 3 are bonded with an adhesive such as a hot-melt adhesive or adhesive means such as a heat seal at end edge portions in the front-rear direction, and the liquid impermeable backsheet 2 laterally protruding from the absorbent body 4 and the side non-woven fabrics 7 are bonded with the adhesive such as the hot-melt adhesive or the adhesive means such as the heat seal at edge portions on both sides. Wing flaps W, W that are protruding both sides, and second wing flaps $W_B$, $W_B$ formed at portions near a buttock side thereof, respectively, are formed by stacked sheet portions of the liquid impermeable backsheet 2 and the side non-woven fabrics 7.

Hereinafter, the structure of the sanitary napkin 1 is further described in detail.

As the liquid impermeable backsheet 2, a sheet material having at least a water shielding property such as polyethylene is used, and recently, a material having moisture permeability is often preferably used to prevent sweating. As the sheet material having such a water shielding property or moisture permeability, a microporous sheet is preferably used that is obtained by forming a sheet by melting and kneading inorganic filler in olefin series resin such as polyethylene or polypropylene and then extruding the sheet in one axial direction or two axial directions. One or a plurality of adhesive layers (not illustrated in the drawings) are formed at a non-using surface side (outer surface) of the liquid impermeable backsheet 2 so that the sanitary napkin 1 can be fixed to an underwear when attached to a body. As the liquid impermeable backsheet 2, a poly-laminate sheet in which a plastic film and a non-woven-fabric are stacked may be used.

Next, as the liquid permeable topsheet 3, a perforated or imperforate non-woven fabric or a porous plastic sheet is preferably used. As a material fiber for constituting the non-woven fabric, in addition to a synthetic fiber including an olefin series such as polyethylene or polypropylene, a polyester series, a polyamide series and the like, a regenerated fiber such as rayon or cupra (cuprammonium rayon), a natural fiber such as cotton may be used. As the non-woven fabric, a non-woven fabric obtained by an appropriate processing method such as a spun lace method, a spun bond method, a thermal bond method, a melt blown method or a needle punch method may be used. Among these processing methods, the spun lace method is superior in terms of great flexibility and drape properties, and the thermal bond method is superior in terms of bulkiness and softness. When a plurality of through holes are formed in the liquid permeable topsheet 3, the body fluid can be rapidly absorbed and a dry touch property becomes good.

The absorbent body 4 provided between the liquid impermeable backsheet 2 and the liquid permeable topsheet 3 is, for example, constituted of cotton-like pulp and absorbent polymer. The absorbent polymer is mixed into the pulp constituting the absorbent body as granular powders, for example. As the pulp, chemical pulp obtained from wood, a cellulose fiber such as dissolving pulp, and an artificial cellulose fiber such as rayon or acetate may be raised, and softwood pulp having a fiber length longer than that of hardwood pulp is preferably used in terms of function and price. Further, a synthetic fiber may be mixed into the absorbent body 4. The synthetic fiber may be, for example, a polyolefin series such as polyethylene or polypropylene, a polyester series such as polyethylene terephthalate or polybutylene terephthalate, a polyamide series such as nylon, a copolymer thereof, or a mixture of two kinds thereof. Furthermore, a composite fiber such as a core-clad type fiber including a core made of a fiber with a high melting point and a clad made of a fiber with a low melting point, a side-by-side type fiber or a division type fiber may be also used. When the synthetic fiber is made of a hydrophobic fiber, it is preferable to treat a surface of the synthetic fiber with a hydrophilic agent so that the synthetic fiber has hydrophilic properties to the body fluid.

The convex portion 20 of an absorbent body that is high toward the skin side is formed along a longitudinal direction at the skin side surface of the absorbent body 4 at a center portion in a width direction. It is preferable that the convex portion 20 has a function to rapidly absorb the body fluid expelled at an upper surface of the liquid permeable topsheet 3, but to release the absorbed body fluid to be permeated in the absorbent body 4 without reserving in the convex portion 20. In order to improve permeability, it is preferable to use a material in which a chemical fiber is mixed in a pulp fiber, an air through absorbent body, an air-laid absorbent body, or a material made of a tow fiber. By mixing the chemical fiber into the convex portion 20, the convex portion 20 can retain its height even when the body fluid is absorbed therein without shrinking and can retain a cushion function. In order to make the convex portion 20 high, and improve fitting to the body, it is preferable to mix the tow fiber (fiber bundle) or a polyester series fiber such as polyethylene terephthalate or polybutylene terephthalate into the convex portion 20.

Here, it is unnecessary for the absorbent body 4 to contain a chemical fiber, and may be formed by a pulp fiber only, or a mixtures of the pulp fiber and a super absorbent polymer. For the absorbent body 4, permeability is not so important, and it is preferable to retain the body fluid permeated from the convex portion 20 not to leak outside, the absorbent body 4 may not contain the chemical fiber.

The absorbent body 4 and the convex portion 20 may be stacked in an assembling step after separately manufacturing, or the absorbent body 4 and the convex portion 20 may be integrally formed by three-dimensionally fiber stacking an absorbent body. Further, a two-stage fiber stacking structure may be used in which the convex portion 20 is fiber stacked on the absorbent body 4.

The convex portion 20 is further described in detail later.

In the sanitary napkin 1, it is preferable to form a pair of center compressed grooves 16 in a lateral direction along an approximately longitudinal direction of the sanitary napkin 1 from an outer surface side of the liquid permeable topsheet 3 to surround the convex portion 20. The center compressed grooves 16 may include at least portions extend along the approximately longitudinal direction of the napkin at both sides of a center line CL in the longitudinal direction, respectively. For the illustrated example, front end portions and rear end portions in the lateral direction are connected with each other, respectively, to be formed into a shape that extends in the napkin longitudinal direction in total, and that is closed in a circumferential direction.

Further, a front compressed groove 16a having substantially a "Ω" shape in a planar view is formed at front of the center compressed groove 16 to be apart from the center compressed groove 16, and a rear compressed groove 16*b* having substantially a reversed "Ω" shape in a planar view is formed at rear of the center compressed groove 16 to be apart from the center compressed groove 16. The front compressed groove 16*a* and the rear compressed groove 16*b* are provided for capturing the body fluids flowing at a front surface of the sanitary napkin 1 forward and rearward, respectively, and surely preventing the leakage of the flowing body fluids.

Figure 2:
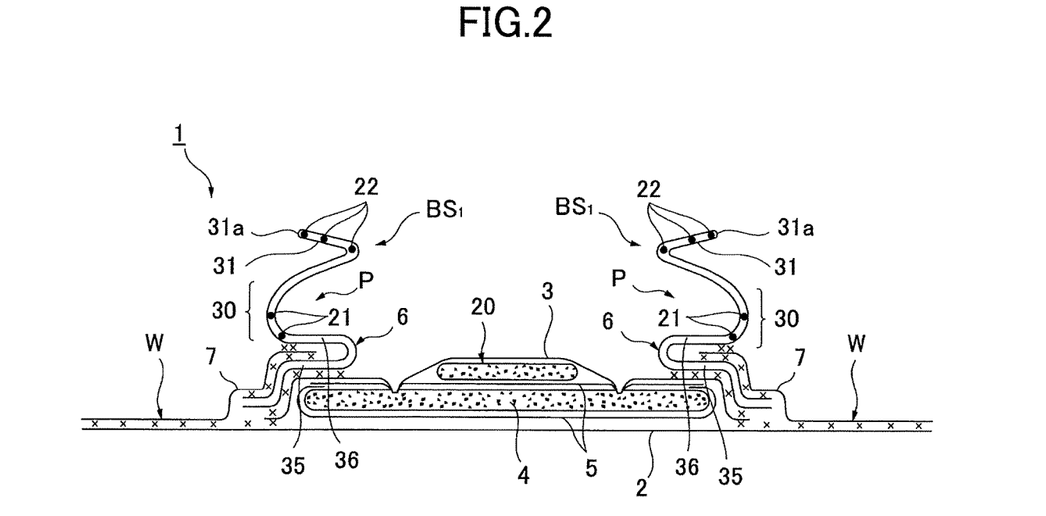
FIG. 2 is a cross-sectional view taken along a II-II line of FIG. 1.
Figure 3:
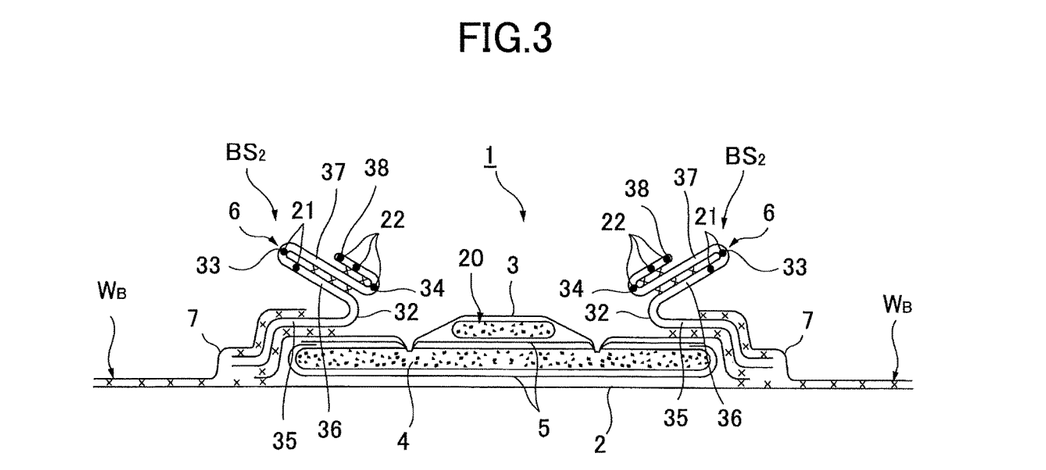
FIG. 3 is a cross-sectional view taken along a III-III line of FIG. 1.

As illustrated in cross-sectional views of FIG. 2 and FIG. 3, for the illustrated example, a width size of the liquid permeable topsheet 3 is slightly longer than a width of the absorbent body 4 to only cover the absorbent body 4. The standing gathers BS are formed by the non-woven-fabrics 6 for forming standing gathers, different from the liquid permeable topsheet 3, and the side non-woven fabrics 7 are stacked on a front surface side of the liquid impermeable backsheet 2 at outsides of the standing gathers BS, respectively. These non-woven-fabrics 6 for forming standing gathers and side non-woven fabrics 7 are constituted by a non-woven-fabric material on which an appropriate water-repellent treatment or hydrophilic process is performed depending on a desired function such as a function of preventing the body fluid from permeating or of improving a texture. As such non-woven-fabrics 6 and 7, one that is formed by an appropriate processing method on a material such as a natural fiber, a synthetic fiber or a regenerated fiber may be used, and preferably, a non-woven-fabric whose basic weight is reduced and has air permeability may be used for eliminating hardness and prevent sweating. Specifically, it is desirable to use a non-woven-fabric manufactured to have a basic weight of 13 to 23 g/m², and it is preferable to use a water-repellent non-woven fabric on which a water-repellent agent of a silicon series, a paraffin series or an alkyl chromic chloride series is coated for surely preventing the permeating of the body fluid.

As illustrated in FIG. 2 and FIG. 3, the side non-woven fabrics 7 are adhered to areas at outer edges of the liquid impermeable backsheet 2 by a hot-melt adhesive or the like. The pair of wing flaps W, W in the lateral direction are formed at side positions of the absorbent body almost corresponding to the body fluid expelling portion, and the second wing flaps $W_B$, $W_B$ are formed at further buttock side positions, by the stacked sheet portions of the side non-woven fabrics 7 and the liquid impermeable backsheet 2. An adhesive layer, not illustrated in the drawings, is provided at an outer surface side of each of these wing flaps W, W and the second wing flaps $W_B$, $W_B$, and when attached to a panties, the wing flaps W, W are bent at positions of folding lines RL, respectively, toward opposite sides to be folded at a crotch portion of the panties to be fixed.

As the non-woven-fabrics 6 for forming standing gathers, a doubly bent sheet is used. A plurality of threadlike elastic stretchable members 21 . . . , and 22 . . . are provided at predetermined positions in this doubly bent sheet at a middle portion in a height direction at both ends or appropriate portions in a longitudinal direction. As illustrated in FIG. 2, the non-woven-fabrics 6 stand at a predetermined area in the longitudinal direction including the blood expelling portion H, and pockets P, P that have openings at an inner side are formed.

Figure 4:
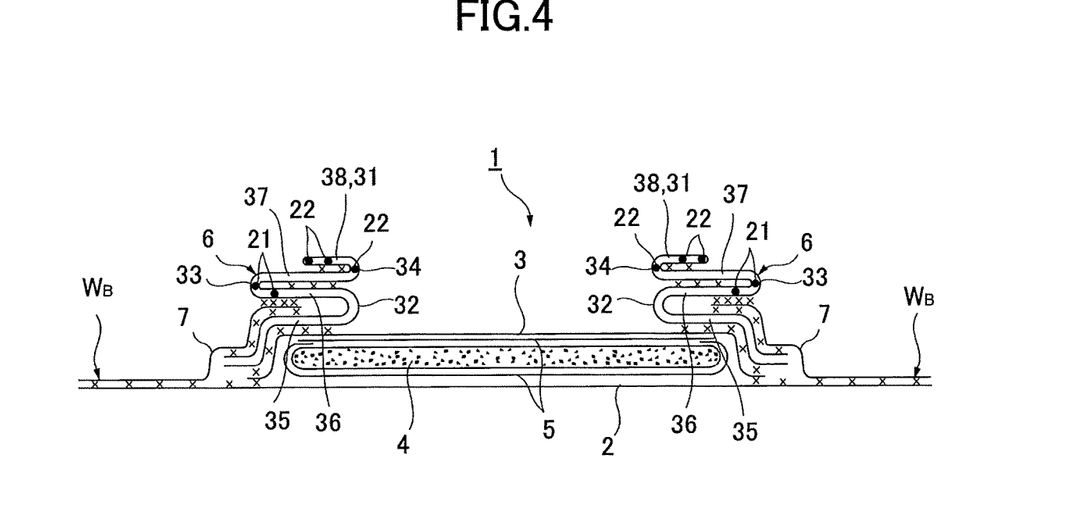
FIG. 4 is a cross-sectional view taken along a IV-IV line of FIG. 1.

Under a folded status illustrated in FIG. 4, each of the standing gathers BS is folded for four times by a first folding portion 32 formed by folding the non-woven-fabric 6 for forming standing gather that extends from an outer side of the napkin 1 in a center direction at a center side position toward an outer side direction, a second folding portion 33 continued from the first folding portion 32 and folded at an outside position toward the center direction and a third folding portion 34 continued from the second folding portion 33 and folded at the center side position toward the outer side, and formed to include a first folded surface 35, a second folded surface 36, a third folded surface 37 and a fourth folded surface 38 in this order from a lower side. Here, the fourth folded surface 38 constitutes a skin contacting surface portion 31.

In the sanitary napkin 1, the standing gathers BS have different standing statuses for front standing gathers $BS_1$ formed at an area including the blood expelling portion H, and rear standing gathers $BS_2$ formed at an area at a buttock side.

As illustrated in FIG. 2, each of the front standing gathers $BS_1$ includes a side standing portion 30 that stands from an outer edge portion of the absorbent body 4 or its vicinity, and the skin contacting surface portion 31, having a predetermined width, formed to be continued from a front edge of the side standing portion 30 and formed substantially horizontal or to be inclined toward a center side with respect to the front surface of the napkin 1, by bonding the second folded surface 36 and the first folded surface 35 and not bonding the other folded surfaces. One or a plurality of threadlike elastic stretchable members that extend along the longitudinal direction of the sanitary napkin 1 with a space therebetween in a standing direction are provided in each of the side standing portions 30 and the skin contacting surface portions 31. For the illustrated example, two threadlike elastic stretchable members 21, 21 are provided in each of the side standing portions 30, and three threadlike elastic stretchable members 22, 22 . . . are provided in each of the skin contacting surface portions 31.

Meanwhile, each of the rear standing gathers $BS_2$ stands toward outer sides from the first folding portions 32 as starting points in a linearly inclined manner, respectively, by not bonding the first folded surface 35 and the second folded surface 36 while bonding the second folded surface 36 and the third folded surface 37, and bonding the third folded surface 37 and the fourth folded surface 38. By providing the front standing gathers $BS_1$ and the rear standing gathers $BS_2$, the fourth folded surfaces 38 of the standing gathers stand to fit a crotch portion of a wearer at a front area including the blood expelling portion H, and the standing gathers that stand in a linearly inclined manner fit along rondure of buttock at a rear area at the buttock side. Thus, standing gathers having high fitting properties that fit shapes of the body at each position can be formed.

(Convex Portion 20)

In the sanitary napkin 1, as illustrated in FIG. 1, the convex portion 20 is constituted by a front convex portion 24 provided at an area including the blood expelling portion H of a wearer, a rear convex portion 25 provided at an area including an intergluteal cleft of the wearer, and a constricted convex portion 23 provided at an area connecting the front convex portion 24 and the rear convex portion 25 in the napkin front-rear direction whose both side edges are constricted toward an inner side. The convex portion 20 is formed in a long and narrow shape along the napkin front-rear direction, and has a planar shape that is laterally symmetry with respect to the center line CL in the longitudinal direction. The convex portion 20 has a configuration in which the front convex portion 24, the rear convex portion 25 and the constricted convex portion 23 are integrally formed as a front end and a rear end of the constricted convex portion 23 are continued from a rear end of the front convex portion 24 and a front end of the rear convex portion 25, respectively.

The front convex portion 24 is formed at the area including the blood expelling portion H of the wearer, specifically, at an area that is slightly longer than the blood expelling portion H at front and rear of the blood expelling portion H. The front convex portion 24 is formed to be vertically long in the napkin front-rear direction, and both side edges of the front convex portion 24 are formed by linear lines extending in the napkin front-rear direction. By forming the front convex portion 24 to be vertically long in the napkin front-rear direction, the front convex portion 24 can easily fit the blood expelling portion H of the wearer easily and the expelled body fluid can be surely absorbed in the front convex portion 24. Further, by forming both side edges by the linear lines extending in the napkin front-rear direction, the body fluid absorbed in the front convex portion 24 can be suppressed from diffusing in the width direction, and the body fluid can easily diffuse in the front-rear direction. If the both side edges are formed by curved lines that bulge outward in the napkin width direction, the body fluid may be concentrated at portions where bulged width becomes the maximum, and the body fluid may flow outside in the width direction therefrom.

A front end edge of the front convex portion 24 is formed by an arc-shaped curve that bulges forward of the napkin. With this, feeling to the skin becomes soft and fit becomes good. The front end edge may be formed in various embodiments such as a line extending in the napkin width direction.

The front convex portion 24 may have substantially the same width along the entire length, and the width may be 15 mm to 40 mm, preferably, may be 20 mm to 36 mm. In the sanitary napkin 1, as the body fluid absorbed in the front convex portion 24 is diffused in the constricted convex portion 23 or in the rear convex portion 25, it is unnecessary to ensure sufficient absorption volume only by the front convex portion 24. Thus, compared with a convex portion that is provided at a body fluid expelling portion of a normal sanitary napkin, the front convex portion 24 can be formed with a narrow width, and diffusion of the body fluid spread in the vicinity of the standing gathers at both side portions can be suppressed.

A rear end of the front convex portion 24 is continued from the constricted convex portion 23. Thus, the body fluid absorbed in the front convex portion 24 can rapidly diffuse in the constricted convex portion 23.

The rear convex portion 25 is formed at the area including the intergluteal cleft of the wearer. Specifically, the rear convex portion 25 is provided at an area from a start position of the intergluteal cleft of the wearer at a crotch side, in a rearward direction, to a position exceeding the intergluteal cleft, an end position of the intergluteal cleft, or a middle position of the intergluteal cleft.

It is preferable that the rear convex portion 25 is formed in a tapered shape whose width is gradually narrowed toward the rear direction of the napkin. With this, the rear convex portion 25 can enter deep inside of the intergluteal cleft, and leakage of the body fluid along the intergluteal cleft can be prevented. Although the tapered shape starts from a front end of the rear convex portion 25 (interface with the constricted convex portion 23) in the illustrated example, the rear convex portion 25 may be formed by linear lines extending in the napkin front-rear direction at both side edges from the front end of the rear convex portion 25 for a predetermined length, and the tapered shape may be started therefrom.

The maximum width of the rear convex portion 25 may be 15 mm to 40 mm, and preferably, may be 20 mm to 36 mm. Further, it is preferable that the maximum width of the rear convex portion 25 and the maximum width of the front convex portion 24 are substantially the same. With this, sufficient absorption volume can be retained at the rear convex portion 25, and the body fluid diffused from the front convex portion 24 can be sufficiently absorbed. As illustrated in FIG. 1, when the tapered shape is formed from the front end of the rear convex portion 25, the maximum width of the rear convex portion 25 is provided at the front end of the rear convex portion 25 (interface with the constricted convex portion 23).

The front end of the rear convex portion 25 is continued from the constricted convex portion 23. Thus, the body fluid absorbed in the constricted convex portion 23 can rapidly diffuse in the rear convex portion 25.

The constricted convex portion 23 is provided at an area connecting the front convex portion 24 and the rear convex portion 25 in the napkin front-rear direction. In other words, the front convex portion 24 and the rear convex portion 25 are provided to be apart from each other in the napkin front-rear direction, and the constricted convex portion 23 connects them. A front end of the constricted convex portion 23 is continued from a rear end of the front convex portion 24, and a rear end of the constricted convex portion 23 is continued from a front end of the rear convex portion 25.

It is preferable that an interface of the front convex portion 24 and the constricted convex portion 23 is provided at an area corresponding to a perineum portion of a wearer. With this, the constricted convex portion 23 can fit a narrow groove or a small concave portion at the skin surface from the perineum portion to the start position of the intergluteal cleft, and flowing of the body fluid along the skin can be prevented.

It is preferable that an interface of the rear convex portion 25 and the constricted convex portion 23 is positioned at the start position of the intergluteal cleft of the wearer at the crotch side or its vicinity. With this, the constricted convex portion 23 can be provided from the perineum portion to the start position of the intergluteal cleft.

The constricted convex portion 23 is formed such that both side edges are constricted toward the inner side. This means that a middle portion of the constricted convex portion 23 is formed to be narrower in the width direction than both edge portions. With this, the constricted convex portion 23 can fit a narrow groove or a small concave portion without a space, leakage of the body fluid that flows along the skin or anxiety against leakage of the body fluid that flows along the skin hardly occurs. It is preferable that a portion of the constricted convex portion 23 that becomes the narrowest is at a center portion of the constricted convex portion 23 in the napkin front-rear direction.

It is preferable that both side edges of the constricted convex portion 23 are formed by arc-shaped curves each having a center at outside in the width direction. With this, as a flow of the body fluid along the arc-shaped curves are generated, diffusion of the body fluid from front to the rear side in the constricted convex portion 23 is hardly prevented, and the constricted convex portion 23 easily fits the skin surface along the body. The arc-shaped curve may be formed by a single arc or a combination of a plurality of arcs having different radiuses of curvature.

In the constricted convex portion 23, it is preferable that a constriction portion that is formed such that both side edges are constricted toward the inner side is formed from the front end of the constricted convex portion 23 (interface with the front convex portion 24) to the rear end of the constricted convex portion 23 (interface with the rear convex portion 25). This means that it is preferable that the entire length of each of the both side edges of the constricted convex portion 23 is formed as an arc-shaped curve having a center at outside in the width direction. With this, each of the both side edges is formed as a moderate arc-shaped curve, and lowering of diffusion of the body fluid hardly occurs.

The minimum width of the constricted convex portion 23 may be 5 mm to 30 mm, preferably, may be 10 mm to 20 mm. The napkin length of the constricted convex portion 23 in the front-rear direction may be 45% to 75%, preferably, 55% to 65% of the length of the front convex portion 24 in the front-rear direction, in consideration of the length from the perineum portion to the start position of the intergluteal cleft at crotch of the body in the front-rear direction. The length of the front convex portion 24 in the front-rear direction may be 70 mm to 100 mm. The total length of the convex portion 20 may be 180 mm to 250 mm.

According to the sanitary napkin 1 configured as described above, as the constricted convex portion 23 is provided between the front convex portion 24 and the rear convex portion 25, the body fluid absorbed in the front convex portion 24 can be diffused over the entirety of the convex portion including the constricted convex portion 23 and the rear convex portion 25. Thus, the body fluid can be efficiently absorbed in the convex portion 20, and the leakage of the body fluid can be prevented. Further, as the body fluid absorbed in the front convex portion 24 diffuses entirety of the convex portion 20 including the constricted convex portion 23 and the rear convex portion 25, and sufficient absorption volume can be ensured by the entirety of the convex portion, it is unnecessary to form the front convex portion 24 to be wide, and the body fluid can be suppressed from being diffused near the standing gathers at both side portions. As a result, a wearer hardly feels anxiety against the leakage.

By providing the constricted convex portion 23, a convex that protrudes toward the skin side is formed at a portion connecting the front convex portion 24 and the rear convex portion 25 as well. Thus, a space is not formed between the skin surface and the front surface of the napkin between the blood expelling portion H and the intergluteal cleft, and the body fluid can be prevented from flowing along the skin. Thus, leakage of the body fluid can be surely prevented, and a wearer can be free from anxiety against the leakage.

Further, as both side edges of the constricted convex portion 23 are formed as constricted toward the inner direction, this constricted convex portion 23 enters a narrow groove or a small concave portion of the body without a space, and flowing of the body fluid along the skin can be prevented.

Generally, it is considered that the convex portion fits the skin surface even when pressure of legs is applied from the napkin width direction when a wearer lies on her side or the like, and an absorption amount of the body fluid is increased, when the width of the convex portion is narrow. However, in such a case, there is a problem that an absorption amount of the body fluid is lowered due to lowering of absorption volume when pressure of legs is not applied from the napkin width direction when the wearer lies on her back or the like, as the width of the convex portion is narrow. In this regard, in the sanitary napkin 1, as the constricted convex portion 23 whose width is relatively narrower than those of the convex portions at front and rear is provided in the convex portion 20, even when the width of the napkin is narrowed due to the pressure of legs when the wearer lies on her side or the like, this narrow constricted convex portion 23 can fit the skin surface, and can absorb the body fluid along the skin surface. Further, when the pressure of legs is not applied in the napkin width direction when the wearer lies on her back or the like, absorption volume can be retained by the front convex portion 24 and the rear convex portion 25, that are relatively wider, and the absorption amount of the body fluid is increased.

As means for forming the constriction portion of the constricted convex portion 23, one of following three means may be used.

First, first means is to fiber stack the convex portion 20 so that the constriction portion is originally formed. With this, the constriction portion is clearly formed and there is a merit that the constriction portion is not deformed after manufacturing the sanitary napkin 1 until it is started to be used. However, there is a defect such as, depending on a shape of the center compressed portions 16 that are provided around the convex portion 20, a space between the convex portion 20 and each of the center compressed portions 16 becomes large, and the convex portion is shifted so that the convex portion does not fit the body, or the shape of the convex portion cannot be easily retained.

Next, second means is to form the constricted convex portion 23 by stacking a convex portion that linearly and continuously formed from the front convex portion 24 to the rear convex portion 25 in which a constriction portion is not formed at both side edges on the absorbent body 4, and compressing to border the above described constriction portion by an emboss. As the emboss, a core emboss may be formed by which the absorbent body 4 and the convex portion are integrally compressed from an outer surface side of the convex portion under a state that the absorbent body 4 and the convex portion are stacked, or a fit emboss may be formed by which the liquid permeable topsheet 3, the convex portion and the absorbent body 4 are integrally compressed from an outer surface side of the liquid permeable topsheet 3 under a state that a stacked body of the absorbent body 4 and the convex portion is covered by the liquid permeable topsheet 3 at a skin side surface. With this, when the fit emboss is formed, there are merits that the constricted convex portion 23 can be easily recognized from outside, and the convex portion 20 is hardly deformed when used. On the other hand, as the constriction portion is formed by compressing the convex portion, there is a defect that the compressed portion is decompressed after the sanitary napkin 1 is manufactured until the product is started to be used, and it is difficult to retain the shape of the constriction portion. Further, as there is a limit in difference in height between the convex portion and the circumferential absorbent body 4, there is a defect that the height of the convex portion toward the skin side is low, and it is hard to fit the skin surface.

Third means is to form the convex portion 20 in which the constricted convex portion 23 is originally formed by fiber stacking, stack the convex portion 20 on the absorbent body 4, and form a fit emboss to border an outer periphery of the convex portion 20 from an outer surface side of the liquid permeable topsheet 3 under a state that the liquid permeable topsheet 3 covers the skin side surface of the convex portion 20. With this, the above described defects of the first means and the second means can be solved, while merits of both of them can be combined such as the constriction portion is hardly deformed, and the convex portion 20 is easily recognized from outside.

Example

As illustrated in Table 1, a test was conducted in which sanitary napkins having convex portions of different shapes were manufactured and absorption amounts of body fluids were compared. A method of the test was to attach a sanitary napkin to a dummy doll that emulates a female body, and to measure an absorption amount of artificial menstrual blood absorbed in the sanitary napkin by observing an attached state under each posture of lie one's right side and lie one's back from outside until artificial menstrual blood is viewed at either one of the standing gathers at both side portions of the sanitary napkin while continuously expelling artificial menstrual blood at a speed of 0.06 cc/s. Here, one minute interval was provided every 20 minutes. The absorption amount was obtained by a difference in weight of the sanitary napkin before and after the test.

For the artificial menstrual blood, a composition including 12.30 weight % of glycerin, 85.18 weight % of ion-exchanged water, 0.45 weight % of CMC (carboxymethyl cellulose sodium), 0.97 weight % of NaCl (sodium chloride), 1.04 weight % of $Na_2CO_3$ (sodium carbonate) and 0.06 weight % of water bloom was used.

Figure 6:
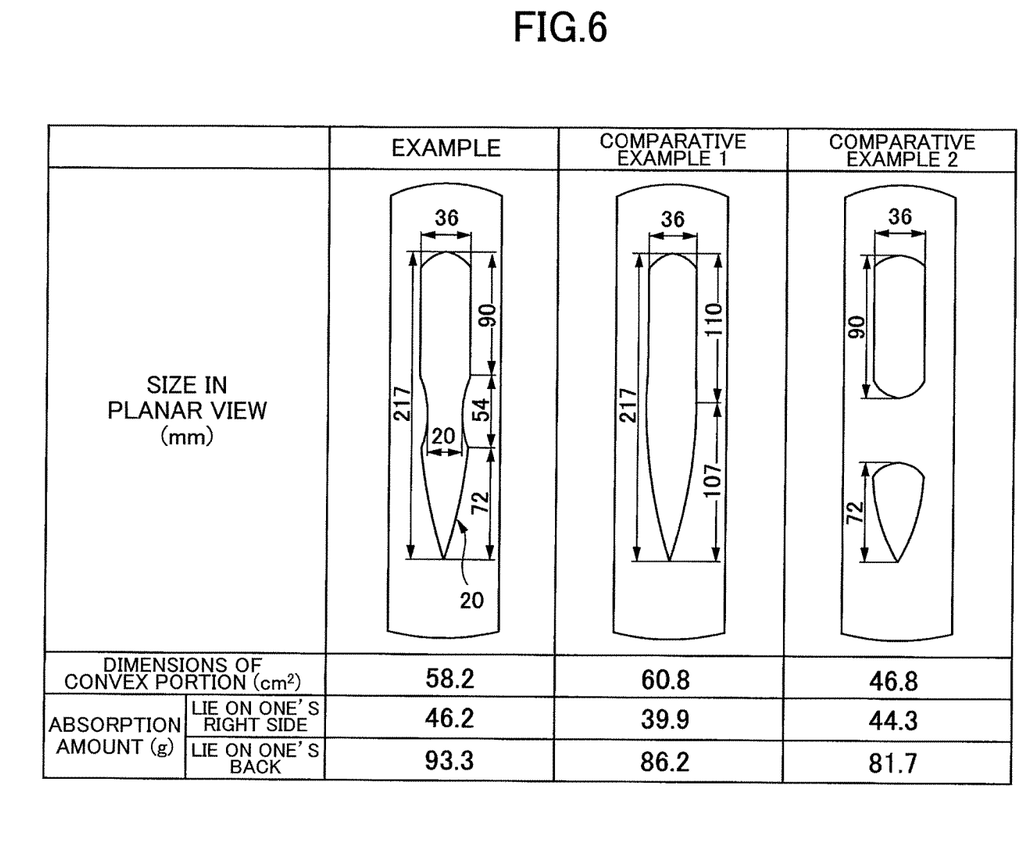
FIG. 6 is a drawing illustrating Table 1.

As illustrated in Table 1 shown in FIG. 6, in the sanitary napkin 1 of example, a result was obtained in which the absorption amount of the body fluid becomes greater compared with each comparative example in both lying postures of lie one's right side and lie one's back. In particular, for a case of lie one's right side, compared with comparative example 1, the absorption amount was increased by 16% in example. With this, it was confirmed that fitting of the convex portion is improved and the body fluid flowing along the skin surface can be absorbed by providing the constricted convex portion 23, even when pressure of legs is applied in the napkin width direction. Further, for a case of lie one's back, compared with comparative example 2, the absorption amount was increased by 14% in example. With this, it was confirmed that the absorption amount of the body fluid was increased by diffusion of the body fluid from the front convex portion 24 to the constricted convex portion 23 and the rear convex portion 25. With this, according to the sanitary napkin 1 of example, leakage can be surely prevented and a wearer hardly feels anxiety against the leakage.

1 . . . sanitary napkin, 2 . . . liquid impermeable backsheet, 3 . . . liquid permeable topsheet, 4 . . . absorbent body, 5 . . . encapsulating sheet, 6 . . . non-woven-fabric for standing gather, 7 . . . side non-woven fabric, 20 . . . convex portion, 23 . . . constricted convex portion, 24 . . . front convex portion, 25 . . . rear convex portion.

What is claimed is:

1. An absorbent article comprising:
    an absorbent body provided between a liquid permeable topsheet and a backsheet, a convex portion of the absorbent body that is high toward a skin side being formed at a skin side surface of the absorbent body at a center portion in a width direction,
    wherein the convex portion includes
        a front convex portion designed to be provided at an area including a body fluid expelling portion of a wearer,
        a rear convex portion designed to be provided at an area including an intergluteal cleft of the wearer, and
        a constricted convex portion provided at an area connecting the front convex portion and the rear convex portion in a front-rear direction of the absorbent article whose both side edges are constricted toward an inner side,
    wherein the front convex portion is formed to be vertically long in the front-rear direction of the absorbent article, both side edges of the front convex portion being formed by linear lines extending in the front-rear direction of the absorbent article, a width of the front convex portion being the same over the entire length, the width of the front convex portion being 20 to 36 mm,
    wherein the rear convex portion is designed to be provided at an area from a start position of the intergluteal cleft of the wearer at a crotch side, in a rearward direction, to a position exceeding the intergluteal cleft, an end position of the intergluteal cleft or a middle position of the intergluteal cleft, a maximum width of the rear convex portion being 20 to 36 mm, the maximum width of the rear convex portion and the width of the front convex portion being the same width, and
    wherein both side edges of the constricted convex portion are formed by arc-shaped curves each having a center at outside in the width direction, an interface of the constricted convex portion with the front convex portion being provided at an area corresponding to a perineum portion of the wearer, a minimum width of the constricted convex portion being 10 to 20 mm, the length of the constricted convex portion in the front-rear direction being 45 to 75% of the length of the front convex portion in the front-rear direction.

2. The absorbent article according to claim 1, wherein the rear convex portion is formed in a tapered shape whose width is gradually narrowed toward a rear direction of the absorbent article.

\* \* \* \* \*